(12) United States Patent
Marquardt et al.

(10) Patent No.: US 7,355,092 B2
(45) Date of Patent: Apr. 8, 2008

(54) **GENETIC VACCINES FOR THE PRODUCTION OF CHICKEN EGG-YOLK ANTIBODIES AGAINST ENTEROTOXIGENIC *ESCHERICHIA COLI* AND OTHER PATHOGENS**

(76) Inventors: Ronald Marquardt, 878 Kilkenny Drive, Winnipeg Manitoba (CA) R3G 4G3; Suk-Hyeon Cho, 212-700 Killarney Avenue, Winnipeg Manitoba (CA) R3T 2N2; Peter Loewen, 1054 des Trappistes, Winnipeg, Manitoba (CA) R3B 1B8; Srinivasa Madhyastha, 71 Loyola Bay, Winnipeg Manitoba (CA) R3G 3J7

( * ) Notice: Subject to any disclaimer, the term of this patent is extended or adjusted under 35 U.S.C. 154(b) by 499 days.

(21) Appl. No.: 10/169,027

(22) PCT Filed: Dec. 27, 2000

(86) PCT No.: PCT/CA00/01583

§ 371 (c)(1),
(2), (4) Date: May 27, 2003

(87) PCT Pub. No.: WO01/48018

PCT Pub. Date: Jul. 5, 2001

(65) Prior Publication Data

US 2004/0087522 A1    May 6, 2004

Related U.S. Application Data

(60) Provisional application No. 60/171,666, filed on Dec. 27, 1999.

(51) Int. Cl.
*C12P 21/00* (2006.01)
*A01K 67/027* (2006.01)
*C12N 15/00* (2006.01)

(52) U.S. Cl. .............................. 800/4; 800/19; 800/21
(58) Field of Classification Search .................. 514/44; 800/19, 21, 4
See application file for complete search history.

(56) References Cited

U.S. PATENT DOCUMENTS

| 4,761,372 A | 8/1988 | Maas et al. |
| 5,620,896 A | 4/1997 | Herrmann et al. |
| 5,891,432 A | 4/1999 | Hoo |
| 5,989,553 A | 11/1999 | Johnston et al. |
| 5,989,584 A | 11/1999 | Cook et al. |
| 6,060,457 A | 5/2000 | Elazhary et al. |
| 6,083,743 A | 7/2000 | Chong et al. |
| 6,100,388 A * | 8/2000 | Casas et al. ............... 536/23.5 |

FOREIGN PATENT DOCUMENTS

| WO | WO 98/14209 | 4/1998 |
| WO | WO 98/17283 | 4/1998 |
| WO | WO 99/04009 | 1/1999 |

OTHER PUBLICATIONS

Marquardt (FEMS Immunology and Med. Microbiol., 1999, vol. 23, p. 283-288).*
Sakaguchi (Vaccine, 1996, vol. 14, No. 8, p. 747-752).*
Beard (Nature Biotech., Dec. 1998, vol. 16, p. 1325-1328).*
Chow (J. Virol., Jan. 1997, vol. 71, No. 1, p. 169-178).*
Jin (FEMS Immunol. Med. Microbiol., 1998, vol. 21, p. 313-321).*
Kim (J. Sci. Food and Agriculture, 1999, vol. 79, p. 1513-1518).*
Kodihalli (J. Virol., May 1997, vol. 71, No. 5, p. 3391-3396).*
Alves, 1998, Immunol. Letters, vol. 62, p. 145-149.*
Alves, Brazilian J. Med. Biol. Res., 1999, vol. 32, p. 223-229.*
Alves, FEMS Immunol. Med. Microbiol., 1999, p. 321-330.*
Turnes, Vaccine, 1999, vol. 17, p. 2089-2095.*
Yokoyama, Infection and Immunity, Mar. 1992, vol. 60, No. 3, p. 998-1007.*
Erhard, J. Vet. Med., 1996, vol. 43, p. 217-223.*

* cited by examiner

*Primary Examiner*—Michael C. Wilson
(74) *Attorney, Agent, or Firm*—Michael R. Williams (57) ABSTRACT

Genetic vaccine which comprises plasmid(s) containing genes coding for antigens of enterotoxigenic *Escherichia coli* (ETEC) strains is disclosed. Additionally, plasmids may consist of multiple copies of the same antigen (i.e. K88 or K99 fimbrial antigen) or multiple antigens (ie. K88 and K99 fimbrial antigens) and genetic adjuvants such as cytokines (IL-2, IL-4 & GM-CSF), costimulatory molecules (CD80 & CD86) or chemokines or immunostimulatory sequences. A method for isolating antibodies from chicken egg yolk for passive immunization of animals, as well as humans to control diarrhoeal diseases using the genetic vaccines is also disclosed.

3 Claims, 9 Drawing Sheets

FIG. 7 a) K88 Sense: 5' GGATCCGGATCCTTAGTAATAAGT 3' (SEQ ID NO. 1)

Anti-sense: 5' AGGGGTTTATGCTAGCAAAAAGACT 3' (SEQ ID NO. 2)

b) K99 Sense: 5' CGCAATGTAGGATCCTTTAAATA 3' (SEQ ID NO. 3)

Anti-sense: 5' CTACTAGCTAGCATCTTAGGT 3' (SEQ ID NO. 4)

GENETIC VACCINES FOR THE PRODUCTION OF CHICKEN EGG-YOLK ANTIBODIES AGAINST ENTEROTOXIGENIC *ESCHERICHIA COLI* AND OTHER PATHOGENS

PRIOR APPLICATION INFORMATION

This application is a national phase application of PCT CA00/01583, filed Dec. 27, 2000 which in turn claims the benefit of U.S. Provisional Application Ser. No. 60/171,666, filed Dec. 27, 1999.

BACKGROUND OF THE INVENTION

Bacteria-mediated diarrhoeal diseases in humans include cholera, typhoid fever, traveller's diarrhoeal and acute diarrhoeal illness in infants (Black, 1993, *Vaccine* 11: 100-106). Typhoid fever is representative of the invasive type which is characterized by invasion of the intestinal mucosa by the pathogen. In the non-invasive type, the symptoms are the result of a bacterial toxin which stimulates an enormous increase in the secretory activity of the cells lining the small intestine causing an acute loss of body fluid. An example of the non-invasive type of pathogen is enterotoxigenic *E. coli* (ETEC), which causes diarrhoea, particularly in children of developing countries and travellers visiting such areas. In fact, this pathogen has recently been identified by the World Health Organization (WHO) as one of the targeted pathogens for control by vaccination (Sansonetti, 1998 *Nature Med* 4: 499-500). In addition to diarrhoeal disease, pathogenic strains of *E. coli* cause urinary tract infections and hamburger disease: urinary tract infections caused by *E. coli* send 1.5 million people to the hospital each year in the United States alone and seven million more to their doctors (Service, 1997 *Science* 276: 533) and the recent outbreaks of hamburger disease in humans caused by *E. coli* 0157:H7 strain (MMWR Morb. Mortal. Wkly. Rep., 1999) are reminders of the ability of bacteria to rapidly adapt to new environmental conditions and new antibiotic counter-measures.

It has also been shown that ETEC-mediated diarrhoeal diseases also affect agricultural animals, especially cattle and pigs. Because calves and piglets are particularly susceptible, the agricultural industry suffers a sizeable loss of livestock each year from outbreaks of these diseases. In the case of piglets, pre-weaning diarrhea occurs shortly after birth from 1 to 7 days of age. In one of the surveys of pre-weaning disease in pigs, diarrhoea had the highest morbidity and represented 11% of the pre-weaning mortality with ETEC being the primary and sole infectious cause (Alexander, 1994 in: Gyles (ed), *Escherichia coli* in domestic animals and humans. (CAB International: Wallingford, UK.), pp. 151-170). A second disease, referred to as post-weaning ETEC diarrhoea typically starts 3 to 10 days after weaning. Otherwise, post-weaning diarrhea occurs after weaning in 22 to 49 day old piglets. This disease is a major cause of economic losses to swine industry from both mortality and reduced growth rates and is the most common cause of post-weaning mortality in many farms, killing 1.5 to 2% of pigs weaned (Hampson, 1994 in: Gyles (ed), *Escherichia coli* in domestic animals and humans. (CAB International: Wallingford, UK), pp. 171-191).

The strains of ETEC that are associated with intestinal colonization are those that express the K88, K99, 987P, F41 and F18 fimbrial adhesions and enterotoxins (Sta, Stb, LT and Vte) (Ojeniyi et al., 1994, *J. Vet Med.* 41: 49-59; Imberechts et al., 1997, *Vet Microbiol* 54: 329-341). These adhesions are located in the rod-like pili (fimbriae) that extend from the *E. coli* and are bound to specific receptors on the intestinal wall. Among the different ETEC, those expressing the K88 fimbrial antigen are the most prevalent form of *E. coli* infection, being found world-wide wherever pigs are raised in high numbers (Rapacz and Hasler-Rapacz, 1986, *Animal Gen* 17: 305-321). Specifically, it has been estimated that K88 ETEC is responsible for 50% of the 10 million piglet deaths each year (Waters and Sellwood, 1982 in: Proceedings of the 2nd World Congress on Genetics Applied to Livestock Production, Madrid, Spain, pp. 362). There are significant concerns that diarrhoea in neonatal and post-weaning pigs will become more serious in the future, given the trend towards large herds, early weaning, increased incidence of antibiotic resistance in microorganisms and pressure by regulatory agencies to ban or reduce the use of antibiotics in feeds. In addition, there is strong evidence to suggest that resistance in an animal pathogen can readily be transmitted to a human pathogen. Clearly, one pathogen that is able to mutate rapidly is *E. coli*, as evidenced by the many antibiotic resistant strains that have appeared. As such, the possibility exists that resistance in livestock pathogens could be transferred to human pathogens. Thus, there is a need to develop alternate strategies to control this organism in human and veterinary medicine, particularly in swine industry.

One of the alternative strategies for controlling the pathogens is vaccination. Traditional vaccines fall into two broad categories: attenuated, non-pathogenic live infectious material; and killed, inactivated, or subunit preparations. Although live attenuated vaccines produce a diverse and persistent immune response, they present safety concerns due to the risk of reversion during replication or mutation to become infectious. Although non-live vaccines do not induce infection, the immunity induced by such vaccines can frequently wane during the life span of inoculated hosts and often requires repeat boosting to achieve lifelong immunity.

Thus to control diarrhoeal diseases in animals and humans, vaccination against specific strains of ETEC using vaccines based on live attenuated or killed organism or recombinant peptide or protein subunit could be an alternative strategy. Use of vaccines based on immunogenic material of *E. coli*, selected from pili, pili proteins and *E. coli* antigens for controlling diarrhoeal disease in livestock has been described by Lutticken, et al., (U.S. Pat. No. 4,788, 056). The most important ETEC virulence associated factors are toxins and colonization factor antigens (CFAs), which are usually fimbrial adhesions on the bacterial surface (Svennerholm et al, 1989, *Vaccine* 7: 196-198). There are several reports on the preparation of genetic vaccines based on colonization factor antigens (CFAs) of ETEC (Alves et al., 1998, *Vaccine* 16: 9-15; Alves et al., 1999, *Brazilian J Med Biol Res* 32: 223-229, Alves et al., 1999, *FEMS Immunol Med Microbiol* 23: 321-330). Specifically, Alves discloses a DNA vaccine for direct vaccination of mice. The vaccine comprises CFA/I fused to glycoprotein D of HSV type 1 virus under the control of Rous Sarcoma Virus promoter. Maas, et al. in U.S. Pat. No. 4,761,372 described the preparation of DNA plasmids containing genes coding for non-toxic heat-labile enterotoxin, non-toxic heat-stable enterotoxin and colonization factor. The plasmids were used to transform *E. coli* and the bacteria containing the plasmids were used as a vaccine.

It is known that the vaccination of a sow against specific strains of *E. coli* results in the secretion of colostrum that will provide passive immunity to the piglets against ingested ETEC. This protection, however, is transient and all protection is lost shortly after weaning. Furthermore, immunization of the piglet is also not practical as colibacillosis will often develop in the piglet before the piglet develops immunity to the inoculum, meaning that direct immunization will not protect such pigs against pathogenic ETEC (Alexander, 1994; Hampson, 1994; Isaacson, 1994 in: Gyles, G. L. (ed), *Escherichia coli* in domestic animals and humans (CAB International: Wallingford, UK), pp. 629-647).

The fimbrial antigens of porcine ETEC that are associated with intestinal colonization have been extensively investigated with respect to their genetic background, protein chemistry, and immunological properties. As discussed above, purified fimbrial antigens (Husband and Serman, 1979, *Austral. Vet. J.* 55: 435436) and recombinant proteins (Isaacson, 1985, *Avian Diseases* 30: 28-36; Gyles and Mass, 1987, *Prog. Vet Microbiol. Immun.* 3: 139-158) have been widely used with promising results as vaccine antigens in controlling colibacillosis in pigs (Isaacson, 1994). In passive immunization experiments, chicken egg-yolk antibodies raised against the different fimbrial antigen when administered orally, have also been shown to be highly effective at protecting neonatal pigs against fatal enteric colibacillosis (Yokoyama et al., 1992, *Infect Immun.* 60: 998-1007; Marquardt et al., 1999, *FEMS Immun. Med. Microbiol.* 23: 283-288). The disadvantages of using protein immunization is that the protein must be purified and injected frequently in the presence of an adjuvant if a high and sustained antibody titre is to be obtained. This is an expensive, time consuming and invasive procedure. In addition, isolation of antigens from human pathogens is potentially dangerous.

One highly attractive and effective alternative approach for the control of pathogens, including *E. coli*, is to use therapeutic antibodies. These antibodies can be produced in any animal and can be administered orally to another animal to control a specific disease. The advantage of using antibodies is that they provide a long term and sustainable means of controlling pathogens. Such a treatment would be highly effective, would not result in the development of resistant strains of pathogens, would spare the use of antibiotics and could be relatively inexpensive. Antibodies can be obtained from several sources including the colostrum of lactating animal, blood of animals, transgenic animals, transgenic plants, hybridoma cell lines, recombinant microorganisms and chicken eggs. Unfortunately, use of antibodies from the colostrum of lactating animals, particularly dairy cattle, is impractical as the colostrum is only produced over a short period of time. Currently, there is no information on the ability of antibodies from spray-dried plasma to counteract different intestinal pathogens and current methods for monoclonal antibody production either in hybridoma cell lines or transgenic animals/plants or recombinant microorganisms are prohibitively expensive.

The chicken egg (especially, yolk of the egg) is recognized as a rich source of specific antibodies (Gassmann, et al., 1990, *FASEB J* 4: 2528-2538; Tokoro, 1992 in U.S. Pat. No. 5,080,895). Tokoro described a method for treating an intestinal infectious disease in a neonatal mammal caused by a pathogenic organism with antibody-containing substance being obtained from the whole egg or albumen of the egg or the yolk of eggs laid by hens which have been immunized using a pathogenic organism as an antigen. This method claimed to be useful in treating diarrhoea in a neonatal mammal caused by ETEC. This suggests the potential of producing more specific antibodies against mammalian antigens in chickens compared to mammals because of the phylogenic distance between birds and mammals, low cost of production and convenience, and more importantly, the compliance with regulations for modern livestock production. Specifically, chickens produce eggs non-invasively and due to the phylogenic distance, the adjuvant does not cause severe responses as it does in mammals. It has also been shown that the production and maintenance of high levels of specific antibodies over a long period of time are possible in laying hens. Also, it is now possible to obtain antigen specific antibodies from egg-yolk of hyper-immunized hens. A hen lays 200-300 eggs per year and one egg yolk contains about 150 mg of antibodies. The yolk or the purified antibody can be dried by freeze-drying or spray-drying without the loss of activity and can be fed directly to the young pigs to provide protection against specific ETEC (Marquardt, et al., 1994 in: New Emerging Ova-Biotechnology (Ed. Sim and Nakai) CAB International: Wallingford, UK). When antibodies raised against ETEC (i.e. K88) fimbrial antigens were administered orally to neonatal and early-weaned piglets, they were protected against ETEC infections (Marquardt, et al., 1999 *FEMS Immunol Med Microbiol* 23: 283-288). It is of note that purified or partially purified peptides were used to elicit the immune response in the host, which served as the source for the antibodies. However, there are certain disadvantages in using fimbrial proteins as antigens for producing antibodies in chicken eggs. Firstly, the specific antibody titre obtained in the egg yolk is only moderate compared to that obtained by using larger proteins as antigens. Secondly, the antigen must be administered to chickens several times in a year of laying cycle so as to maintain high antibody titre. Therefore, the production of antibodies using fimbriae as antigens is relatively expensive.

Clearly, a more effective, less costly method of producing anti-ETEC antibodies in chickens for use in passive immunization is needed.

SUMMARY OF THE INVENTION

According to a first aspect of the invention, there is provided a method of producing eggs containing anti-fimbrial antibodies comprising: providing a hen; providing a genetic vaccine comprising a promoter functional in chicken cells operably linked to a nucleic acid sequence encoding a fimbrial antigen; administering the genetic vaccine to the hen; promoting expression of the fimbrial antigen in the hen; and collecting eggs laid by the hen.

According to a second aspect of the invention, there is provided a method of producing anti-fimbrial antibodies comprising: providing a hen; providing a genetic vaccine comprising a promoter functional in chicken cells operably linked to a nucleic acid sequence encoding a fimbrial antigen; administering the genetic vaccine to the hen; promoting expression of the fimbrial antigen in the hen; collecting eggs laid by the hen; and isolating the antibody-containing fraction from the eggs.

According to a third aspect of the invention, there is provided a method of producing a feed additive containing anti-fimbrial antibodies comprising: providing a hen; providing a genetic vaccine comprising a promoter functional in chicken cells operably linked to a nucleic acid sequence encoding a fimbrial antigen; administering the genetic vaccine to the hen; promoting expression of the fimbrial antigen in the hen; collecting eggs laid by the hen; and drying the eggs, thereby producing a powder.

According to a fourth aspect of the invention, there is provided a genetic vaccine comprising: a promoter functional in chicken cells operably linked to a nucleic acid sequence encoding a fimbrial antigen.

DESCRIPTION OF THE PREFERRED EMBODIMENTS

Unless defined otherwise, all technical and scientific terms used herein have the same meaning as commonly understood by one of ordinary skill in the art to which the invention belongs. Although any methods and materials similar or equivalent to those described herein can be used in the practice or testing of the present invention, the preferred methods and materials are now described. All publications mentioned hereunder are incorporated herein by reference.

Definitions

As used herein, "genetic vaccine" refers to a nucleic acid molecule engineered to express an antigenic peptide for eliciting an immune response in a host.

As used herein, "vector" refers to the genetic backbone for the genetic vaccine.

As used herein, "fimbrial antigen" refers to fimbriae, fimbrial proteins, fimbrial protein subunits, and immunogenic epitopes of fimbrial protein subunits.

As used herein, "genetic adjuvant" refers to nucleic acid sequences that will enhance the humoral immune response, for example, cytokines, chemokines or costimulatory molecules and other immunostimulatory sequences. The cytokines may be, for example, interferons, interleukins, GM-CSF, G-CSF or tumour necrosis factors.

As used herein, "multivalent vaccine" or "multivalent vector" refers to a vector or vaccine containing two or more inserted sequences, for example, tandem copies of a fimbrial antigen, copies of two or more different fimbrial antigens, or at least one fimbrial antigen and at least one genetic adjuvant.

As used herein, "passive immunity" refers to the transfer of antibodies from a donor to a recipient.

As used herein, "multiple cloning site" refers to a region within the vector containing a plurality of restriction enzyme sites.

Described herein are genetic vaccine vectors for immunizing a host against ETEC antigens. The vaccines comprise a promoter functional in the intended host operably linked to a nucleic acid sequence encoding at least one E. coli fimbrial antigen. The fimbrial antigen may be, for example, K88, K99, 987 P, F41 or F18. Alternatively, as discussed below, antigens from other pathogenic microorganisms may be used. The vector may also include genetic adjuvant sequences for eliciting a specific immune response pattern. The genetic adjuvants may be, for example, IL-2, IL-4, GM-CSF or costimulatory molecules CD80 and CD86. The vaccine is administered to the host using means known in the art so that the vaccine enters the cells of the host wherein the fimbral antigen is expressed. As the fimbrial antigen is expressed, the host animal produces antibodies against the fimbrial antigen(s) as part of the host's immune response. It is of note that the genetic vaccine is more stable than traditional peptide-based antigens, which are degraded by host proteases. In embodiments wherein the host is for example a chicken, these antibodies are present in eggs laid by the chicken.

Use of a genetic vaccine containing specific genes coding for antigens of pathogenic E. coli and/or other pathogenic microorganisms provides an efficient, cost-effective and safe alternative for producing antibodies which can be used in controlling diarrhoeal and other infectious diseases. This technology allows specific genes to be expressed in non-replicating vectors (Chattergoon, et al., 1997). The sequence of a plasmid insert can be manipulated to present all or part of the genome of an organism of interest, thereby tailoring the immune response to the pathogen. Also, genes that lead to undesired immunogenic inhibition or autoimmunity can be altered or deleted together. Furthermore, genes that encode important immunologic epitopes can be included whereas those that confer pathogenicity or virulence can be excluded. This flexibility can be exploited to include sequences of multiple epitopes within a protein or across divergent sequences from different strains. Furthermore, immunity to multiple epitopes and/or multiple organisms be achieved within a single construct.

It is known that the immune response to genetic vaccine can also be manipulated by altering the conditions under which the vaccine is administered (Fynan et al., 1993 Proc Natl Acad Sci USA 90: 11478-11482; Cox and Coulter, 1997, Vaccine 15: 248-256; Boyle et al., 1998, DNA & Cell Biol 17: 343-348; Eriksson et al., 1998, J Surgical Res 78: 85-91; Cohen et al., 1998, FASEB J 12: 1611-1626; Lewis and Babiuk, 1999 Adv Virus Res 54: pp. 129-188). These conditions include the method of delivery (through gene gun, microneedles, liposomes, microspheres, adenovirus and attenuated bacteria), route of administration (intradermal, intramuscular, intranasal and oral), presence of immunostimulatory sequences (ISS), the immunization regimen, the co-administration of cytokines or chemokines or costimulatory molecules and also the administration of endotoxin-free DNA vaccine.

Thus, immunization with nucleic acids (genetic immunization) offers conceptual advantages over live attenuated, killed or inactivated organism, recombinant peptide, and protein based vaccines (Chattergoon et al., 1997, FASEB J 11: 753-763; Barry and Johnston, 1997, Vaccine 15: 788-791; Weiner and Kennedy, 1999, Scientific American, 7: 50-57). Specifically, the DNA vaccine allows the sustained expression of the antigen, whereas peptide-based antigens are degraded over time.

First, in contrast to other types of vaccines, genetic immunization allows the antigen to be intracellularly synthesized directly in the host. Second, genetic vaccination does not require tedious protein production and purification procedures. Furthermore, the purified peptide may be denatured or extremely labile. Third, the development of vectors for genetic immunization provides an elegant system to manipulate the local cytokine environment at the immunization site, thereby directing a distinct T-cell response pattern. Fourth, microgram quantities of DNA vaccine can induce both humoral and cellular immune responses. Fifth, multiple vectors or a multivalent vector encoding several antigens can be delivered in a single administration, as discussed above. Sixth, the use of DNA from a highly virulent pathogen (i.e. 0157:H7 *E. coli*) as an antigen for immunization is unlikely to pose any danger to humans.

EXAMPLE I

Bacterial Strains and Growth Condition

*E. coli* strains I294 and I297, which were provided by Dr. R. E. Isaccson (Iowa state University, Iowa, USA), contained the plasmids used for the synthesis of the fimbrial gene. Specifically, strain I294 has the K88 ac fimbrial gene inserted into the HindIII site of a pBR322, while strain I297 has the K99 fimbrial gene inserted in the BamHI site (Isaacson, 1985, *Avian Diseases* 30: 28-36). *Ecoli* NM522 was used for transformation experiments and for isolation of plasmid DNA, as discussed below. Bacteria were grown in Luria broth or Luria agar with ampicillin (50 ug/ml).

EXAMPLE II

Vaccine Construction

Referring to the drawings, vaccines were constructed using a plasmid as the vector. In this example, the plasmid is pPSLIATP (provided by Dr. Lorne Babiuk, Veterinary Infectious Disease Organization, University of Saskatchewan, Saskatoon, Canada). The vector includes a multiple cloning site for insertion of coding sequences as described below downstream of the human cytomegalovirus (hCMV) intermediate early promoter. In addition, between the multiple cloning site and the hCMV promoter is an intron for promoting transport of the transcribed mRNA out of the nucleus. It is of note that the intron is upstream of the multiple cloning site so that protein synthesis is not affected by the presence of the intron. Downstream of the multiple cloning site is a polyadenylation sequence from bovine growth hormone. Thus, as a result of this arrangement, coding sequences inserted into the multiple cloning site will be transcribed by the hCMV promoter and polyadenylated. In addition, upstream of the multiple cloning site is a tissue plasminogen activation site which promotes production of the insert, as described below.

As discussed above, in some embodiments, the antigen coding sequences are selected from fimbrial antigens, for example, K88, K99, 987P, F41, F18 or combinations thereof. It is of note that other fimbrial antigens known in the art including those from other pathogenic organisms may also be used. In addition, the coding sequences may include genetic adjuvants for directing a distinct T-cell response pattern. The genetic adjuvants may be selected from, for example, IL-2, IL-4, GM-CSF and costimulatory molecules CD80 and CD86.

Figure 1:
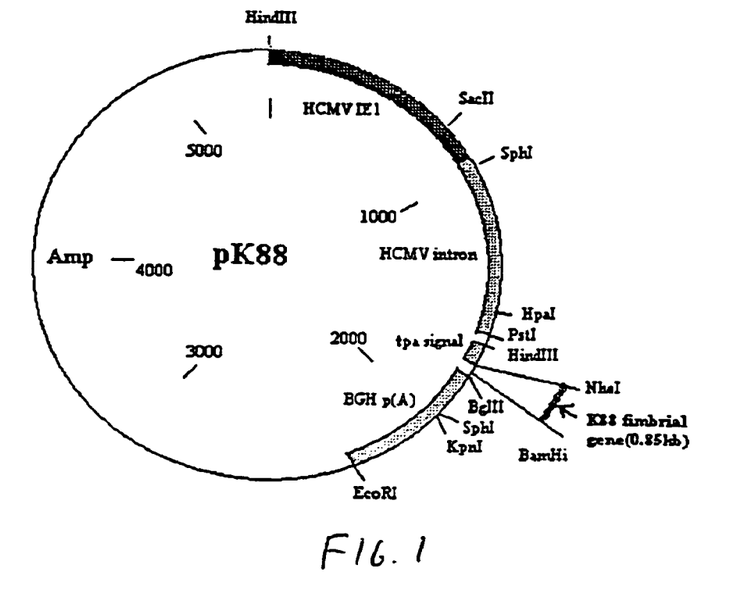
FIG. 1 is a plasmid map of pK88.
Figure 2:
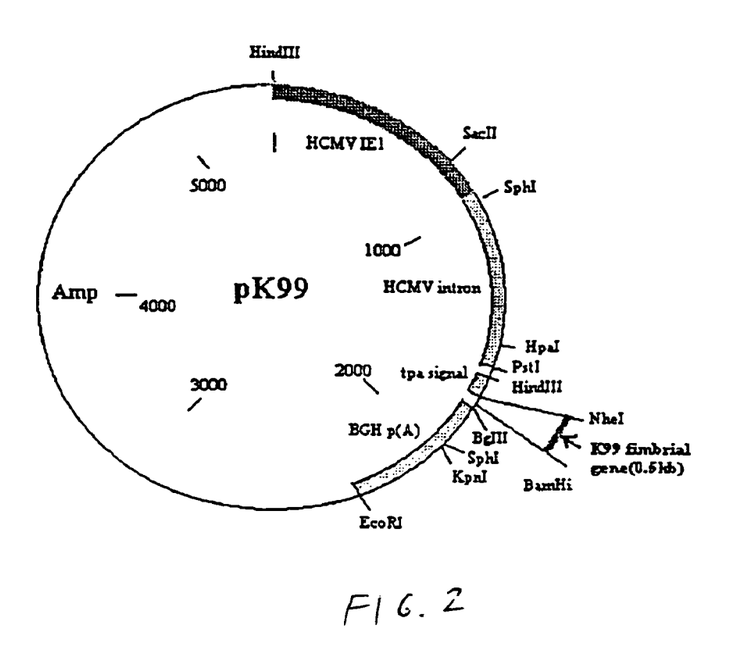
FIG. 2 is a plasmid map of pK99.
Figure 3:
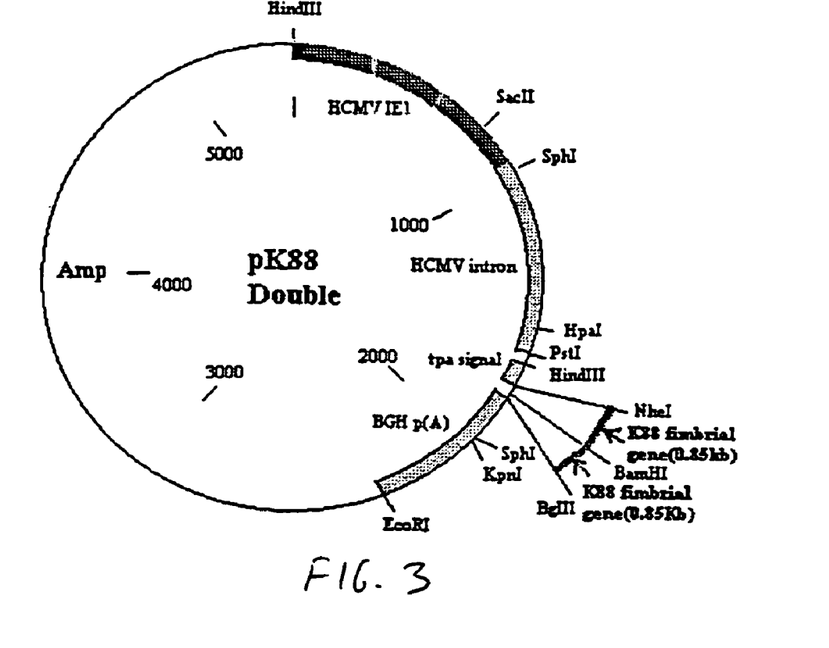
FIG. 3 is a plasmid map of pK88-Double.
Figure 4:
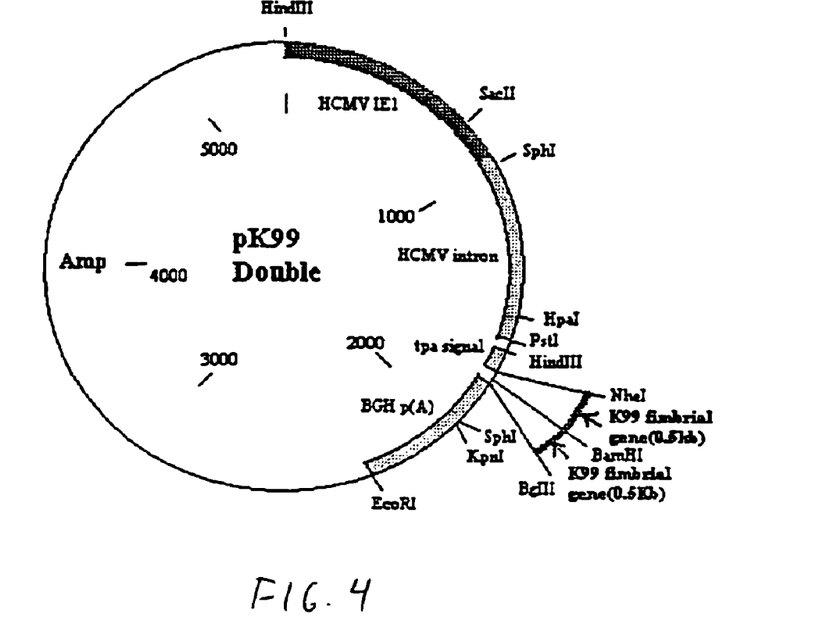
FIG. 4 is a plasmid map of pK99-Double.
Figure 5:
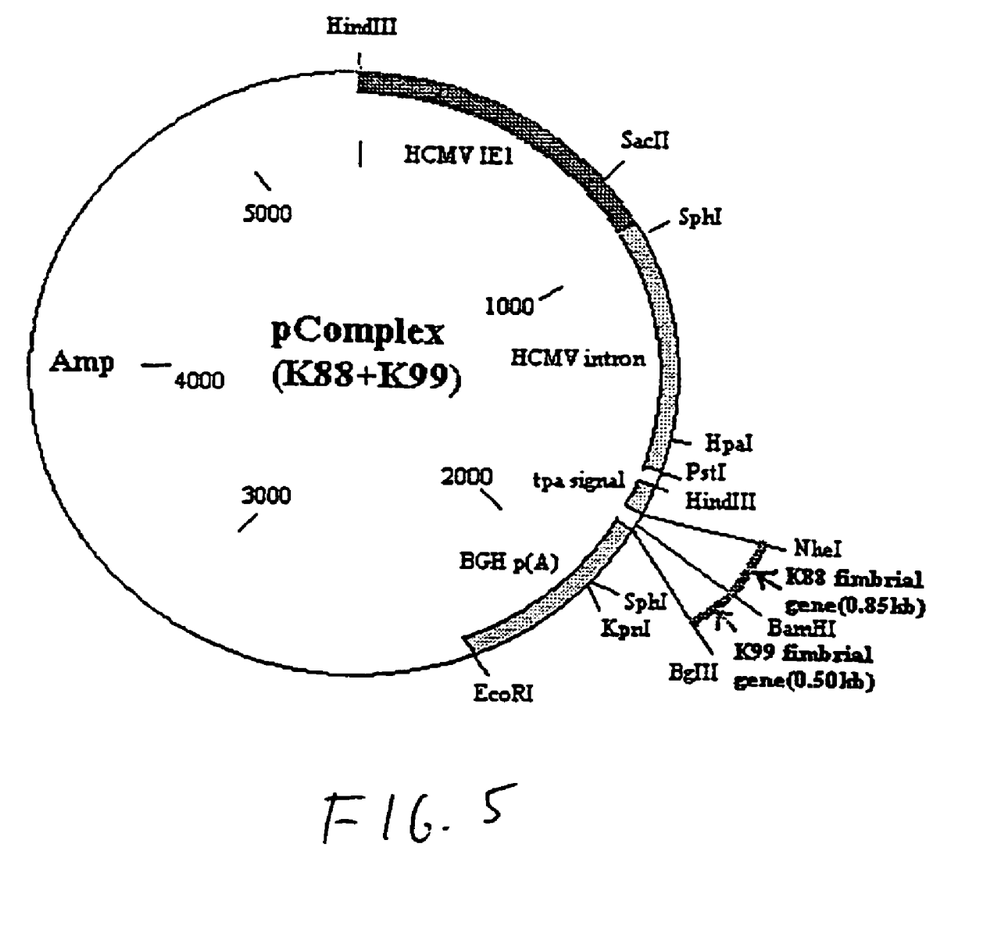
FIG. 5 is a plasmid map of pComplex.
Figure 6:
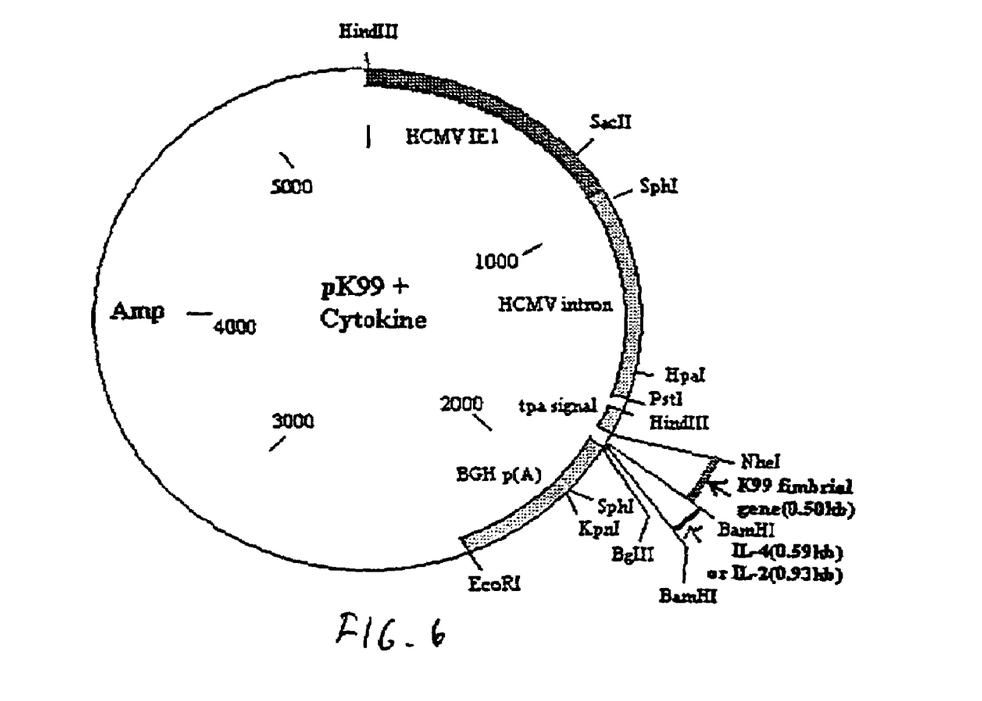
FIG. 6 is a plasmid map of pK99+Cytokine.
Figure 7:
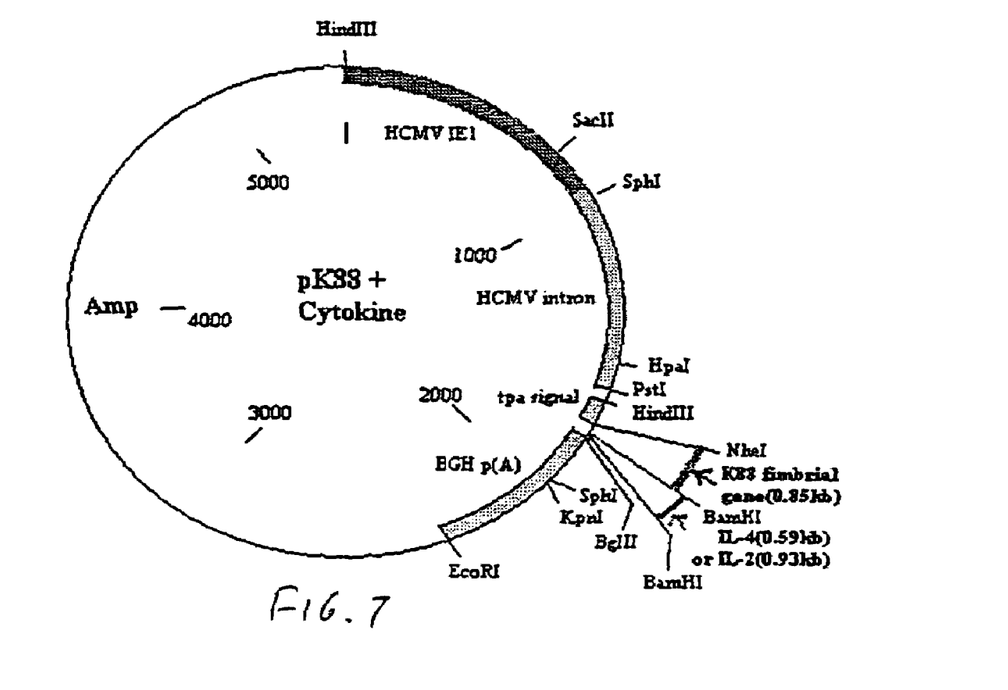
FIG. 7 is a plasmid map of pK88+Cytokine.
Figure 8:
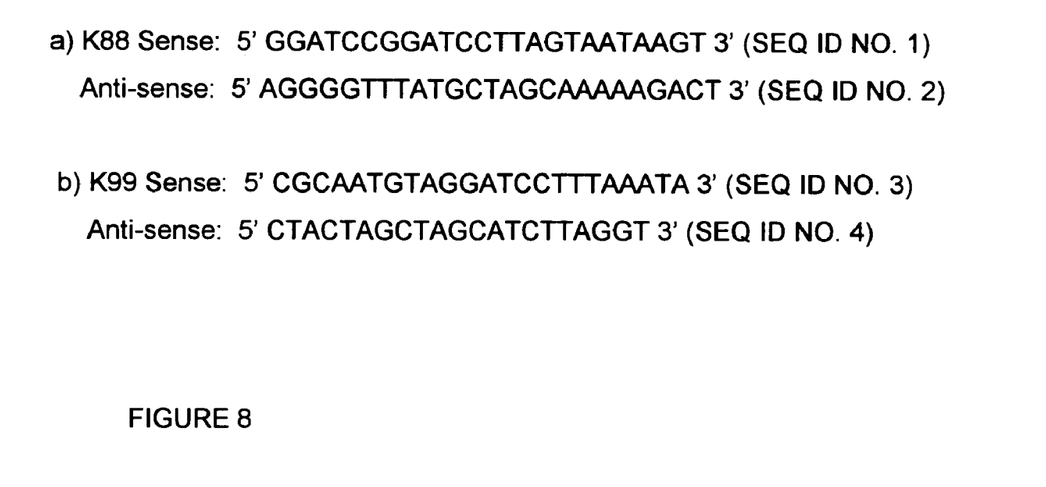
FIG. 8 shows the primers used for PCR synthesis.
Figure 9:
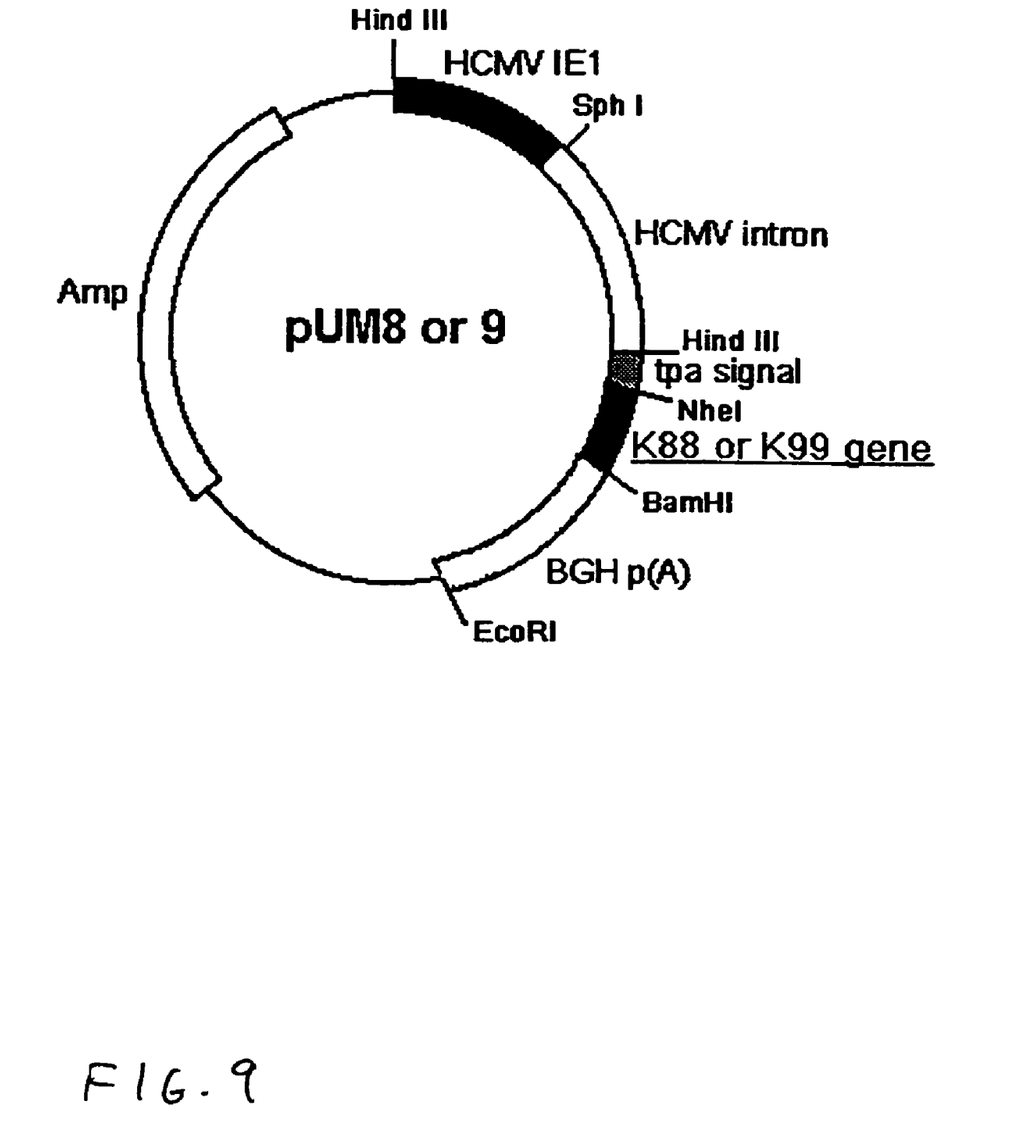
FIG. 9 shows the plasmid maps of pUM8 and pUM9.
Figure 10:
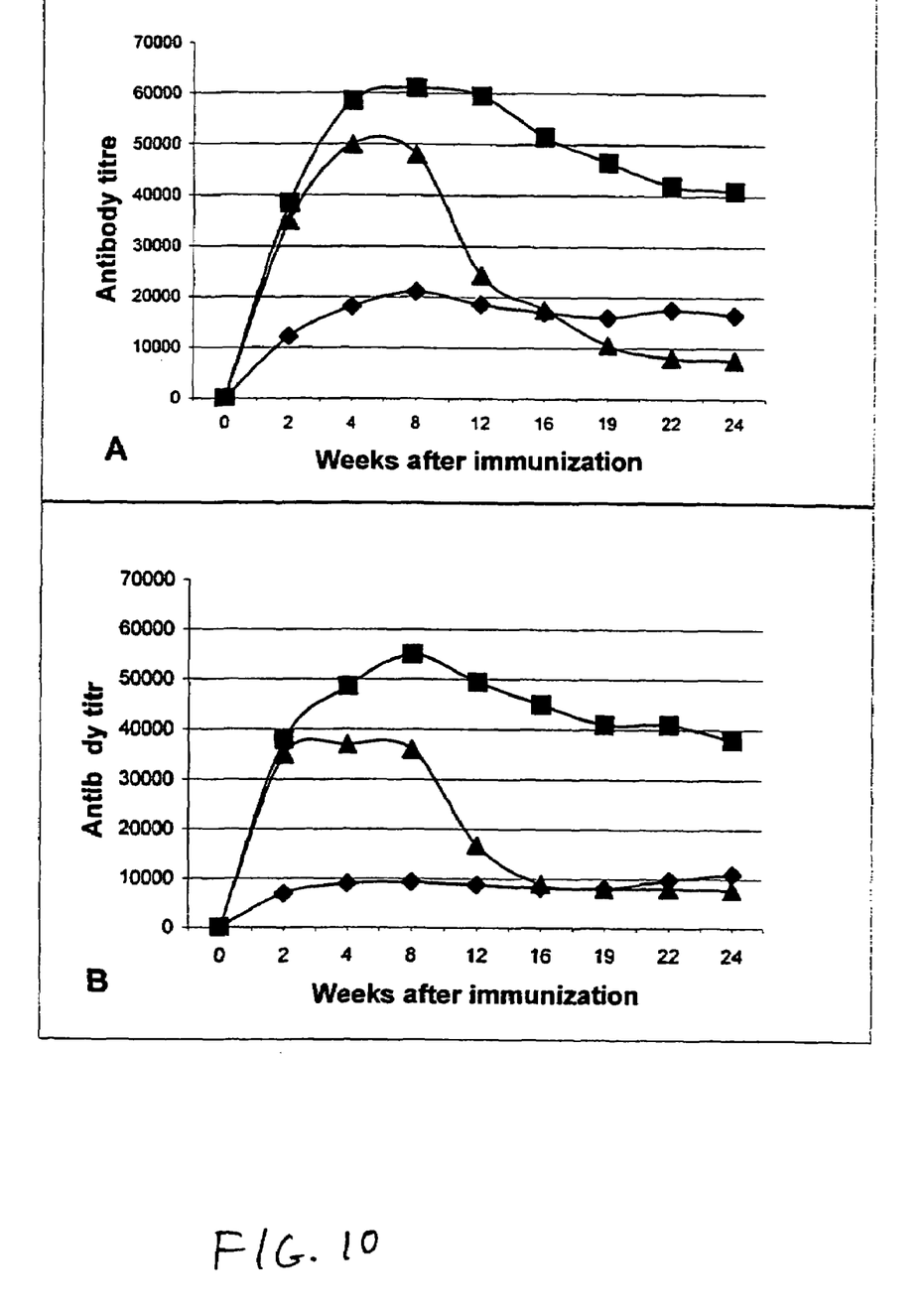
FIG. 10 shows serum antibody response of immunized mouse against K88 (A) and K99 (B) fimbrial adhesions as determined by ELISA. (■) represents combined injection of DNA and protein, (▲) represents protein alone and (♦) represents DNA alone.

As shown in the drawings, *E. coli* fimbrial antigens are inserted into the multiple cloning site and, in some examples, genetic adjuvants are inserted into the multiple cloning site adjacent to the fimbrial antigens. Specifically, as shown in FIG. 1, in pK88, the *E. coli* K88 fimbrial gene is inserted in the multiple cloning site of pPSLIATP; as shown in FIG. 2, in pK99, the *E. coli* K99 fimbrial gene is inserted in the multiple cloning site of pPSLIATP; as shown in FIG. 3, in pK88-Double, two copies of the *E. coli* K88 fimbrial gene are inserted in the multiple cloning site of pPSLIATP; as shown in FIG. 4, in pK99-Double, two copies of the *E. coli* K99 fimbrial gene are inserted in the multiple cloning site of pPSLIATP; as shown in FIG. 5, in pComplex, the *E. coli* K88 and K99 fimbrial genes are inserted in the multiple cloning site of pPSLIATP; as shown in FIG. 6, in pK99+Cytokine, the *E. coli* K99 fimbrial gene and either IL-2 or IL-4 are inserted in the multiple cloning site of pPSLIATP; and, as shown in FIG. 7, in pK88+Cytokine, the *E. coli* K88 fimbrial gene and either IL-2 or IL-4 are inserted in the multiple cloning site of pPSLIATP. As shown in FIG. 9, the fimbrial gene, encoding the CFA/I protein, was amplified by polymerase chain reaction (PCR) using as template total DNA of the ETEC strains I294 and I297 and two pairs synthetic oligonucleotide primers containing restriction sites for Nhe I and Bam HI, respectively (SEQ ID Nos 1-4, shown in FIG. 8). The product of the PCR reaction was electrophoresed on a 0.8% agarose gel and recovered with glass beads (Bio 101. Inc., Canada). Fragments were ligated into the appropriate restriction sites in the expression vector. The resulting plasmids, named pUM8 and pUM9, containing the K88 and K99 fimbrial antigens coding sequences, respectively, were used to transform competent *E. coli* NM522. The pUM8 plasmid expressing the K88ac colonization factor antigen contained a fragment of approximately 0.85-kb between Nhe I and Bam HI. In the case of *E. coli* strain K99, plasmid pUM9 had a fragment of about 0.55-kb at the same site as pUM8 (FIG. 10). The plasmid DNA was purified and the concentration of plasmid DNA was determined at 260 nm. Before injection, the plasmid was precipitated in ethanol, washed with 70% (vol./vol.) ethanol, and dissolved in sterilized saline. It is of note that these examples are provided for illustrative purposes and are in no way limiting. As will be apparent to one knowledgeable in the art, further details of the constructs are shown in the drawings.

EXAMPLE III

Purification of Fimbriae

*E. coli* strains I294 and I297 were cultured for 36 h at 37° C. in 1-L of LB broth with 25 ug/ml of ampicillin. Cultures were centrifuged at 4° C. and 3000 g for 15 min, and the pellets were resuspended with 5-ml of PBS (pH 7.2). The precipitates were heated to 60° C. in a water bath for 30 min to release the fimbriae from the bacteria and, while still hot, were blended for 10 min at high speed using an IKA-ULTRA-TURRAX T25 homogenizer (Jacke & Kunkel GmbH & Co IKA Labortechnik, Staufen, Germany). The insoluble bacteria residue was removed by centrifugation (14,000 g, 4° C., 15 min), and after filtering through a 0.45-um membrane filter (Millipore Corp, Milford, Mass. 01757, USA). Citric acid (2.5%) was added to the supernatant to a pH of 4.0 to precipitated the fimbrial. The fimbriae were allowed to precipitate at 4° C. for 2 h and then collected by centrifugation (14,000 g, 4° C., 15 min). The precipitated fimbriae were resuspended and dissolved in 5-ml of PBS folloewed by precipitation by adding 2.5% citric acid to pH 4.0. The pH 4.0 precipitation and solubliztion steps were repeated three times. The final pellet was dissolved in 0.1 M PBS and store at −20° C. at a concentration of about 1.0-mg fimbriae protein/ml.

EXAMPLE IV

Immunization of Mice

A total of 40 female CD-1 mice (4-6 weeks) were randomly assigned to two groups (K88 and K99 groups), each containing 20 mice. These mice were then further allocated to 4 groups of 5 mice each and each group was injected with DNA alone, fimbrial protein alone, DNA and protein combined and an expression vector only control. Five mice were injected at two weeks intervals intramuscular (i.m.) once each time into the tail skin with 100 ug of plasmid DNA dissolved in 100 ul of PBS (pH 7.2) using 27-gauge needles. For protein immunization, five mice were injected intramuscularly at 2-weeks intervals twice each time with 100-ug in 100-ul PBS of purified fimbrial protein emulsified in an equal volume of Freund's complete adjuvant. The second boost of the fimbrial protein (100 ug) was mixed with Freund's incomplete adjuvant. For mixed immunization, five mice were injected with both plasmid DNA and fimbrial protein emulsified in Freund's complete adjuvant or incomplete adjuvant each at the same time. The amounts of DNA and protein injected were as described above. Blood (300 ul) was collected from the tail at 2-weeks intervals after immunization and immediately incubated at 4° C. for 2 h and centrifuged to obtain serum. Serum was stored at −20° C. until assayed for antibody titre.

EXAMPLE V

Immunization of Laying Hens

Twelve-week old chickens (total 64) were divided into four group of 8 chickens each. Each group was given the DNA vaccine alone, fimbrial protein alone, DNA plus protein simultaneously, and controls (expression vector alone and 0.85% saline alone). Two DNA inoculations were given, one at time zero and the second 2-weeks later, to each of 8 chicken in the same group. DNA (100 ug) was administered in 1-ml of saline using a 27-gauge needle. For protein immunization, chickens were injected with 500-ug of the fimbrial protein in one ml emulsified in an equal volume of Freund's complete (day 0) or incomplete (week 2) adjuvant at 0 and 2 weeks after immunization, and 250-ug/ml of protein emulsified in an equal volume of Freund's incomplete adjuvant was administered at 4 week after immunization. This injection protocol for protein injection was also used as for the DNA plus protein immunization. In addition, there are two different controls. Eight of chicken were injected the expression vector without the inserted gene, and another 8 chickens were injected with 0.85% saline emulsified in adjuvant to act as a control of protein immunization. Egg yolk samples were collected at 2-week's intervals after immunization up to 24-weeks. The eggs were cracked, the yolks were separated from the white and the yolk were diluted 10 times in pH 7.2 PBS to measured antibody titre using ELISA.

EXAMPLE VI

Detection of Antibodies by ELISA

Enzyme-linked immunosorbent assay (ELISA) with purified fimbrial antigen was used to analyze the sera of immunized mice or egg yolk of immunized chicken. Wells of MicrotestIII flexible assay plates were coated at 4° C. for overnight with 0.1 ug of the fimbrial antigen suspended in PBS. After overnight blocking at room temperature with 5% w/v skin milk in PBS and washings with PBS-0.05% Tween 20 (PBS-T), plates were inoculated with dilutions of mice sera or egg yolk and kept for 2 h at 37° C. After washing, alkaline phosphatase conjugated goat anti-mouse IgG (Jackson ImmunoResearch Inc., 1:5,000) or alkaline phosphatase conjugated rabbit anti-chicken IgY (Jackson ImmunoResearch Inc., 1:5,000) was used as the second antibody, for 2 h at 37° C. The reaction was visualized with the commercial tablets containing substrate (Sigma), after 40 minutes at 37° C. The $A_{405}$ of the reactions were determined in a microplate reader (Bio-Rad, Model 3550, Richmond, Calif., USA, 94804). The titre was the dilution of antibody required to give one-half of the maximum absorbance reading. Assays at different times were corrected using a standard sample containing known K88 or K99 antibody titres.

EXAMPLE VII

Immune Responses in Mice

Figure 11:
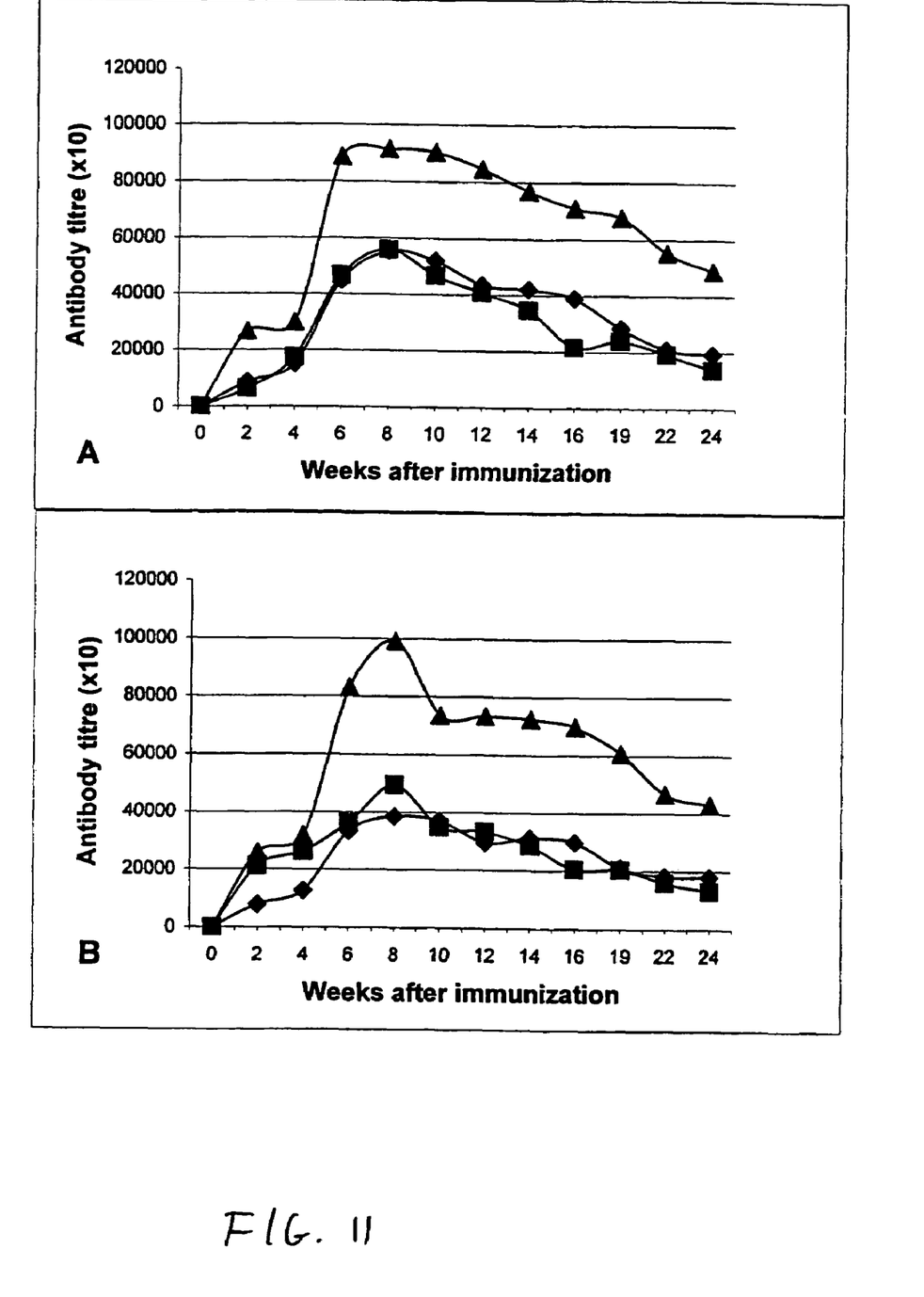
FIG. 11 shows egg yolk antibody response against K88 (A) and K99 (B) fimbrial adhesions of immunized lying hens as determined by ELISA. (■) represents combined injection of DNA and protein, (▲) represents protein alone and (♦) represents DNA alone.

The time course change in antibody titre for K88 and K99 fimbrial proteins in mice that were administered the DNA plasmid alone, fimbrial protein alone or both DNA and fimbrial protein are outlined in FIG. 11. The results show that when either fimbrial protein was injected alone, there was a dramatic increase in the titre of K88 and K99 antibodies within 4 weeks of the $1^{st}$ immunization followed by a gradual decrease in titre over the following 24 weeks. Mice injected with DNA reached a peak titre within 6-8 weeks which only slightly decreased over the next 16 to 18 weeks. The maximum titre obtained with DNA alone was about three (K88) or four (K99) fold less than that obtained with fimbrial protein alone. However after 24 weeks the titre obtained with both types of vaccines were similar. The combined injections of both DNA and protein yielded the highest titres, typically within 8 weeks of injection and then decreased by less than 35% over the following 16 weeks. The titres obtained after 24 weeks with the combined injections were approximately 3 to 4 fold higher than those obtained when either K88 or K99 DNA or fimbrial protein was injected alone. No antibodies against K88 and K99 were detected in mice prior to injection or in the controls. It is of note that the highest and longest sustained titre was obtained when both antigen and DNA was injected.

EXAMPLE VIII

Immune Responses of Chicken

Figure 12:
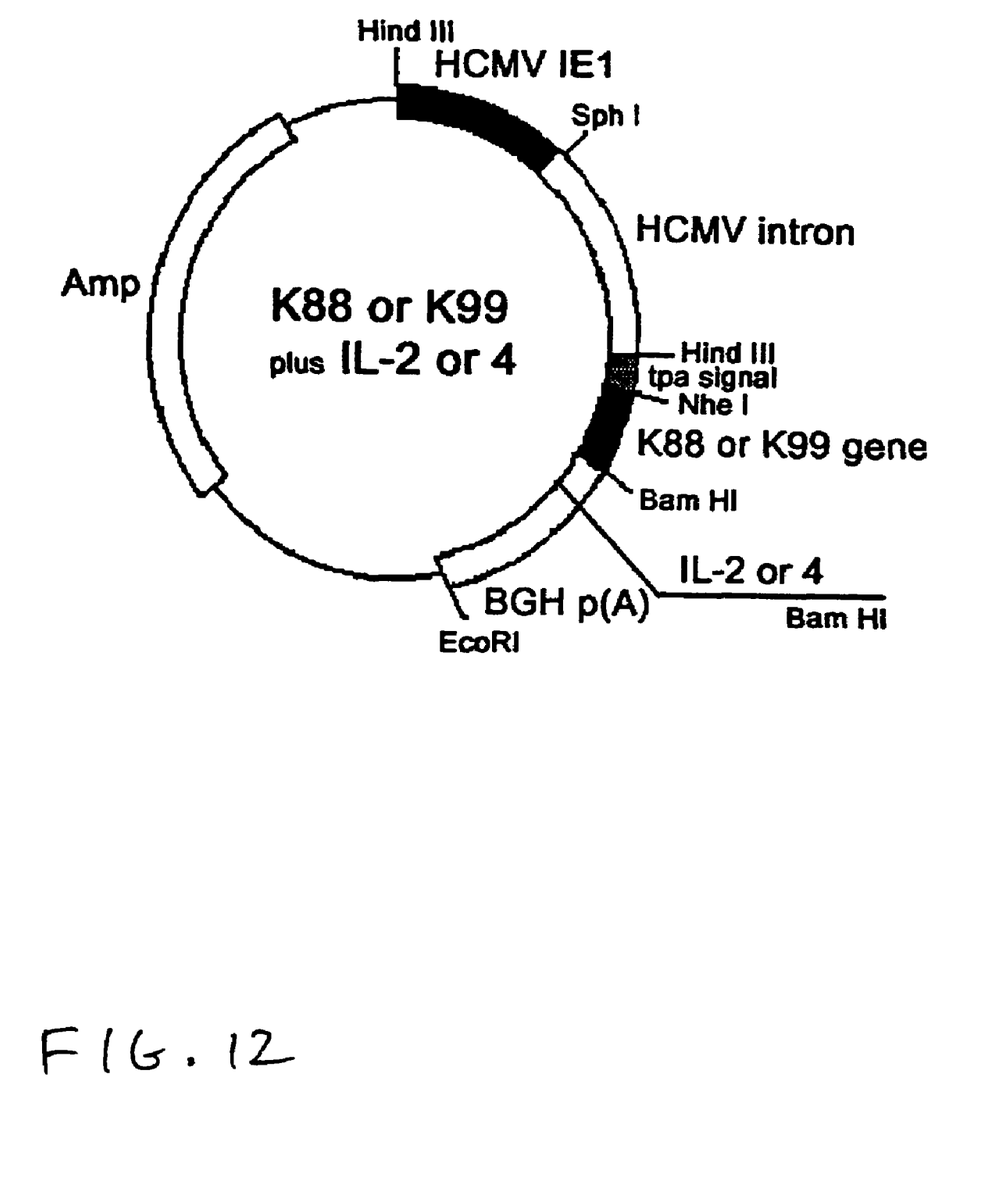
FIG. 12 is the plasmid map of combined vaccine having K88 or K99 inserted adjacent to IL-2 or IL-4.

The pattern of response of antibody production in the yolk of eggs from laying hens immunized with K88 or K99 fimbrial antigens, a DNA plasmid that can express these antigens or both the fimbrial antigens and then corresponding DNA vaccine is shown in FIG. 12. The pattern is similar for each antigen (K88 and K99) and to that obtained with the mouse model. These results demonstrate that the injecting a DNA vaccine in combination with a protein can greatly enhance immune response in animals. Injection of the both the fimbrial antigen and its DNA plasmid yielded K88 and K99 antibody titers that were 2 to 2.5 times greater than that obtained with either DNA or the protein antigens alone. Also the titer with the combined injection after 24 weeks that was nearly equal to the maximum values obtained after 8 weeks with either DNA or protein alone.

EXAMPLE IX

Conclusion

The data demonstrated that the same DNA vaccines can be used to elicit an antibody responses in both mammalian (mice) and avian (chicken) species. Furthermore, co-injection of a DNA vaccine plus its corresponding antigen elicits production of a higher titer of antibodies than that obtained by either the DNA plasmid or protein alone.

EXAMPLE X

Administration of Vaccine

Hen chickens, in this embodiment, 20-week old White Leghorn laying hens (Shaver SX 288) are injected with any one of the above-described genetic vaccines (for example, 50-100 ug) intramuscularly or intradermally. Alternatively, the vaccine may be administered orally. It is of note that delivery of the genetic vaccine can be facilitated by the use of means known in the art, for example, liposomes, microspheres, a gene gun, microneedles, attenuated *Salmonella typhimurium* or modified adenovirus. If necessary, the immunization can be repeated, for example, two weeks later, often using the same dose and inoculation procedures. As described above, following administration of the vaccine, the vaccine enters the cells of the chicken. Therein, the hCMV promoter drives transcription of the mRNA encoding the fimbrial antigen (and the genetic adjuvant). The transcript is then translated, producing fimbrial antigen within the cells of the chicken. As a result, the immune system of the chicken produces antibodies against the fimbrial antigen, which are present in the eggs laid. Eggs are collected and if necessary, antibodies are isolated from the egg yolk as previously described by Marquardt et al. (1999). It is of note that whole egg, the albumen or yolk of the egg or the purified IgY— antibody containing fraction can be used for the therapeutic or preventative control of infectious diseases including diarrhoea. The whole eggs or fractions can be dried and fed to animals such as pigs, bovine species, chickens, pets or to humans. The antibodies can also be used for assaying antigens, microorganisms or intestinal receptors capable of binding the microorganisms from which the antigenic sequences were obtained.

EXAMPLE XI

Titration of Antibody-Containing Material

The titre of the egg-yolk antibody can be tested by direct enzyme-linked immunosorbent assay (ELISA). For example, the wells of a 96-well microplate are coated by adding 100 µl of K88 or K99 or 947P or F41 or F18 fimbrial antigen (0.5 µg per well in 0.1 M bicarbonate buffer, pH 9.6), and incubating overnight at 4° C. The contents of the wells are then aspirated and the plate is washed three times with PBS buffer containing 0.05% Tween 20 (PBST). The wells are filled with 175 µl of blotto (5%, w/v; skimmed dry milk powder in PBS, pH 7.4) and the plate is incubated at 30° C. for 2 h to block non-specific binding sites. After 5-7 rinses with PBST, 100 µl of the egg-yolk extracts (50 µg protein per ml) are added to each well in a series of triple dilutions. The microplate is then incubated at 37° C. for 2 h. After washing with PBST, 100 µl of alkaline phosphatase conjugated antibody (rabbit anti-chicken IgY) are added to each well and incubated at 37° C. for 2 h. The plate is washed 5 times with PBST and 100 µl of alkaline phosphatase substrate solution (1 mg/mL p-nitrophenol phosphate in diethanolamine buffer, pH 9.8) is added to each well. The plate is incubated at room temperature until a strong colour is developed and the reaction is stopped by the addition of 100 µl of 5 M NaOH to each well. The optical density of the wells is determined at 405 nm with an ELISA reader.

Costimulatory molecules, also known as costimulatory ligands, when present in antigen-presenting cells, act to stimulate helper T cells (type 2), which in turn produce IL-4 and IL-6, which stimulate B-cells, which in turn produce antibodies. Stimulating any portion of this pathway also acts to repress the cytotoxic T-cells (type 1) which are involved in a different segment of the immune response.

In other embodiments, other vectors, for example, engineered virus vectors, artificial chromosomes and the like, may be used.

In other embodiments, nucleic acid sequences coding for antigens of other pathogenic microorganisms may be inserted into the genetic vaccine or the vector described above. These may include, for example, genes encoding antigens of *E. coli* strains causing mastitis in cattle, urinary tract infections and hamburger disease in humans, as well as antigens from *Vibrio cholerae, Clostridium* spp., *Campylobacter* spp., *Salmonella* spp., *Klebsiella* spp., *Cryptosporidium* spp., *Yersinia* spp., *Shigella* spp., *Helicobacter pylori, rotaviruses, coronavirus, enteric adenovirus, astrovirus, calicivirus* and other pathogenic microorganisms.

It is of note that dried or non-dried whole egg, albumen, yolk of or purified fraction of the egg containing antibodies from chickens immunized using the above-described genetic vaccine can be used to control diarrhoea and various other infectious diseases in animals and humans. In addition, the purified antibodies can be used in diagnostics or as additives in cosmetics and medicines.

It is of note that in the above-described embodiments, transcription of the fimbrial antigen is driven by an hCMV promoter. It is of note that other viral promoters, such as promoters from Rous Sarcoma Virus or SV40. The advantage of using viral promoters is that it provides the flexibility to use the vaccine in a variety of species. However, in other embodiments, strong chicken promoters may also be used.

As discussed above, the vaccine may be, in some embodiments, a multivalent vaccine, wherein two or more fimbrial antigens or a tandem copy of a single fimbrial antigen or one or more fimbrial antigens and one or more genetic adjuvants are inserted into the vector. As discussed above, multiple copies of the fimbrial antigen produces more antigen than a single copy. Furthermore, as discussed above, the inclusion of the genetic adjuvant in the same vaccine or vector as the fimbrial antigen not only allows for the manipulation of the local immune response, but also ensures that the genetic adjuvant and the fimbrial antigen are expressed and presented in the same cell. Specifically, using multiple, univalent plasmids, each containing a different fimbrial antigen and/or genetic adjuvant leaves to random chance that all of the necessary elements will be present in a single cell. This is of particular importance when costimulatory molecules are used as the genetic adjuvant, as discussed above.

While the preferred embodiments of the invention have been described above, it will be recognized and understood that various modifications may be made therein, and the appended claims are intended to cover all such modifications which may fall within the spirit and scope of the invention.

The invention claimed is:

1. A method of producing eggs containing anti-fimbrial antibodies comprising: providing a hen; providing a genetic vaccine comprising a vector having a promoter functional in chicken cells operably linked to: (a) a nucleic acid molecule encoding K88 fimbrial antigen; and (b) a nucleic acid molecule encoding IL-2; administering the genetic vaccine to the hen; collecting eggs laid by the hen after expression of the K88 fimbrial antigen in the hen, wherein said eggs contain anti-K88 antibodies.

2. The method of claim 1 further comprising isolating an antibody-containing fraction from said eggs.

3. A method of producing eggs containing anti-fimbrial antibodies comprising: providing a hen; providing a genetic vaccine comprising a vector having a promoter functional in chicken cells operably linked to: (a) a nucleic acid molecule encoding K88 fimbrial antigen; and (b) a nucleic acid molecule encoding IL-2; administering the genetic vaccine and a k88 protein antigen to the hen; collecting eggs laid by the hen after expression of the anti-K88 antibodies in the hen, wherein said eggs contain said anti-K88 antibodies.

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: Description of Artificial Sequence: plasmid
    primers

<400> SEQUENCE: 1
ggatccggat ccttagtaat aagt                                          24

<210> SEQ ID NO 2
<211> LENGTH: 25
<212> TYPE: DNA
<213> ORGANISM: Artificial Sequence
<220> FEATURE:
<223> OTHER INFORMATION: Description of Artificial Sequence: plasmid
    primers

<400> SEQUENCE: 2
aggggtttat gctagcaaaa agact                                         25

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: plasmid
    primers

<400> SEQUENCE: 3
cgcaatgtag gatcctttaa ata                                           23

<210> SEQ ID NO 4
<211> LENGTH: 21
<212> TYPE: DNA
<213> ORGANISM: Artificial Sequence
<220> FEATURE:
<223> OTHER INFORMATION: Description of Artificial Sequence: plasmid
    primers

<400> SEQUENCE: 4
ctactagcta gcatcttagg t                                             21